US006926708B1

(12) United States Patent
Franks-Farah et al.

(10) Patent No.: US 6,926,708 B1
(45) Date of Patent: *Aug. 9, 2005

(54) FEMALE CLEAN INTERMITTENT CATHETER SYSTEM

(75) Inventors: Judith Franks-Farah, Northbrook, IL (US); Shirley P. Grey, Wauconda, IL (US)

(73) Assignee: Careguide Systems, Inc., Gurnee, IL (US)

( * ) Notice: Subject to any disclaimer, the term of this patent is extended or adjusted under 35 U.S.C. 154(b) by 358 days.

This patent is subject to a terminal disclaimer.

(21) Appl. No.: 09/879,230

(22) Filed: Jun. 11, 2001

Related U.S. Application Data

(60) Provisional application No. 60/211,151, filed on Jun. 13, 2000.

(51) Int. Cl.[7] .......................... A61M 27/00; B65D 69/00
(52) U.S. Cl. ...................................... 604/544; 206/571
(58) Field of Search .................... 604/544, 327–331; 206/216, 570, 571

(56) References Cited

U.S. PATENT DOCUMENTS

| | | | | |
|---|---|---|---|---|
| 5,931,303 A | * | 8/1999 | Salvadori | 206/570 |
| 6,090,075 A | * | 7/2000 | House | 604/172 |
| 6,238,383 B1 | * | 5/2001 | Karram et al. | 604/544 |
| 6,248,343 B1 | * | 6/2001 | Jampani et al. | 424/405 |
| 6,640,976 B1 | * | 11/2003 | Franks-Farah et al. | 206/571 |

* cited by examiner

Primary Examiner—John J. Calvert
Assistant Examiner—C. Lynne Anderson
(74) Attorney, Agent, or Firm—Bell Boyd & Lloyd, LLC

(57) ABSTRACT

A method and system for intermittent female catheterization by a patient a patient's caregiver, or a health care provider are revealed. The system contains apparatus for at least one intermittent female catheterization and includes at least one female catheter, antibacterial soap, a lubricant, a mirror, step-by step instructions, and a container, where the above named items are positioned inside the container. The method includes self-care documentation for a medical professional to instruct a patient in the use of the system and to keep a record that the instruction of the patient was performed.

19 Claims, 8 Drawing Sheets

Fig 2A  ~34

Clean Intermittent Catheterization for Women CAREGUIDE® Step-by-Step

*This guide is to be followed only on the order of a physician. This guide is not a substitute for your healthcare professional's instructions. Everything you need to get started for self care is in this kit. The name of each item is on the map on the inside box cover. Find each item in the box before you begin. Keep everything in the box until the guide tells you to use it*

Prepare for Care

Get a clean, fresh towel. Wash your hands with the Antibacterial Soap and warm water. Dry your hands on the clean towel. If you have a caregiver to do this for you, they should wash hands and put on the Gloves

Spread a clean paper towel for a work surface. If you are going to do the procedure on a bed, chair or other furniture, put the Underpad under your buttocks. Take out the Collection Basin and put it between your legs.

Clean "Down"

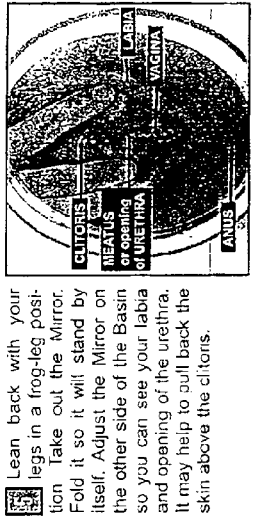

Wet the Paper Wash Cloth with warm water and squeeze approximately a dime size drop of Antibacterial Soap. Lather up about one half of the Cloth. Put it on a corner of the paper towel.

Lean back with your legs in a frog-leg position. Take out the Mirror. Fold it so it will stand by itself. Adjust the Mirror on the other side of the Basin so you can see your labia and opening of the urethra. It may help to pull back the skin above the clitoris.

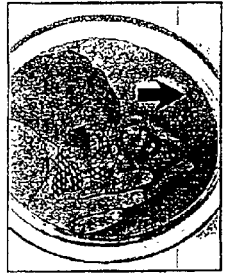

Separate the labia with your first and middle finger of one hand while with the other hand, washing from above the opening of the urethra to the area above the anus

Roll the Catheter

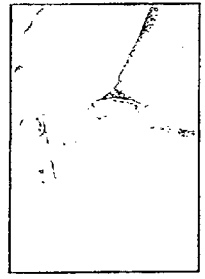

Take the Catheter out of the package or "Clean Catheter" Bag and lay it on a clean paper towel within reach.

Flip open the tube of Lubricating Jelly Be careful not to let the tube touch the Catheter Squeeze about 2 inches of Jelly onto the Catheter, starting at the tip

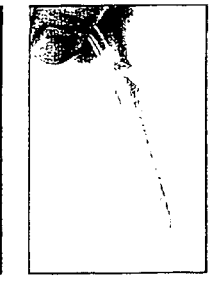

Hold the Catheter so the Jelly touches the paper towel Roll the Catheter in the Jelly to cover all sides

*Always wash from the top to the back. Use a clean area of the Wash Cloth each time. This keeps germs from the anus getting into the urethra. Wash "down" 3 times, then rinse with the other half of the Cloth that has no soap. Throw it away.*

*Continued on the back of this page...*

Fig 2B

Clean Intermittent Catheterization for Women CAREGUIDE Step-by-Step

Insert the Catheter

 Continue holding the labia apart with one hand. With the other hand, pick up the Catheter right behind the Jelly. Watch that you keep the other end of the Catheter in the Collection Basin.

Take a deep breath, hold it and gently put the Catheter tip into the urethra. Push backward and upward until the urine begins to come out. Push the Catheter in another inch. Make sure the urine is running into the Collection Basin When urine stops coming, gently push down on the bladder area to make sure the bladder is empty. Slowly pull the Catheter out. Wipe off any jelly on your body with toilet paper.

 Check the level of urine in the Collectible Container. Write the amount on the Urine Record Card and anything else you want to tell your nurse or doctor.

Clean Up for Next Time

 Wash the Catheter with two or three drops of Antibacterial Soap and warm water. Hold the Catheter under running tap water to rinse well, inside and out. Shake gently several times to get off extra water. Put it on a clean paper towel to air dry

 Empty the Collection Basin. Wash theBasin with 2 drops of Antibacterial Soap and warm water. Rinse well and dry it. Put the cap back on the tube of Lubricating Jelly. Put all the supplies back in the box. Throw away the Underpad if it is dirty

 The Catheter should be dry by now. Close it inside the Plastic Bag marked "Clean Catheter Storage."

*The caregiver may take off the gloves now and wash hands.*

WHEN YOU TRAVEL. In the Fanny Pack, put one clean Catheter in the "Clean Catheter" Bag, for every 4 hours you expect to be away. Also put in the Travel Wipes, the "Used Catheter" Bag, a packet of Lubricating Jelly, and clean paper towels for each catheterization. Take the Alcohol Gel for your handwashing in case there is no water. Follow the same steps above, starting with "Wash your hands." in a private place.

When you take the Catheter out, rinse it if possible and store in it the "Used Catheter" Bag. Wash your hands. When you are home again, clean the Catheter thoroughly and store in the "Clean Catheter" Bag.

Fig 3A ~34A

Cateterización Intermitente para la mujer CAREGUIDE™ Paso a Paso

*Esta guía debe ser usada solamente bajo el consentimiento de su doctor. Esta guía tampoco substituye las instrucciones médicas de su doctor o enfermera. Todos los productos necesarios para empezar el procedimiento están en esta caja. El nombre de cada objeto está adentro de la caja en la tapa. Encuentre cada uno antes de empezar. Mantenga todo en la caja hasta que la guía le diga cuando usarlo. Lea esta guía por completo antes de empezar el procedimiento.*

Preparativos

Busque una toalla limpia y fresca. Lávese las manos con el Jabón antibacterial y agua tibia. Séquelas solo con la toalla limpia. Si tiene a una persona ayudándola, el o ella debe de ponerse los Guantes después de haberse lavado las manos.

Use una Toalla de papel limpia para trabajar sobre ella. Si Ud. va a hacer el procedimiento en la cama, la silla u otro mueble, ponga las Telas de proteger debajo de su recto. Saque el Cofre de coleccionar orina y colóquelo en medio de sus piernas.

El Catéter

- Saque el Catéter de su empaquetaje o de la Bolsa de "catéteres limpios" y colóquelo sobre una toalla de papel cerca de su alcance.
- Abra el pomo de Jalea para lubricar. Tenga cuidado de no tocar el Catéter con el pomo. Exprima 2 pulgadas de jalea en el Catéter, empezando por la punta fina.
- Sostenga el Catéter de manera que la Jalea toque la toalla de papel. Mueva el Catéter en forma circular para que se llene de jalea por todos lados.

Limpieza

- Moje el Paño para lavarse con agua tibia. Exprima una gota de Jabón aproximadamente del tamaño de un centavo. Mezcle el Jabón solo en una mitad del paño. Coloque el Paño en una esquina de la toalla.

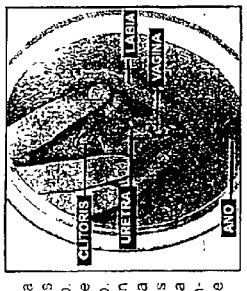

- Recuéstese hacia atrás con sus piernas abiertas. Saque el Espejo. Póngalo en posición que se pueda parar solo. Coloque el Espejo a un lado del Cofre de manera que Ud. pueda ver sus labios y la abertura de la uretra. Le ayudaría sostenerla a un lado la piel que cubre el clítoris.

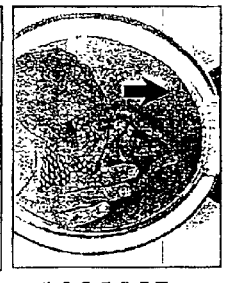

- Separe los labios usando el primer dedo y el del medio de una mano, mientras que con la otra limpia desde arriba de la abertura de la uretra hasta antes de llegar al ano.

*Siempre limpie de arriba hacia abajo, cada vez usando una area del paño que este limpia para lavarse. Este método previene que el sucio del area del ano entre en la uretra. Limpie hacia abajo 3 veces, después remójese con la otra mitad del paño que no tiene jabón ni ha sido usada. Coloque a un lado el Paño. El Paño puede ser lavado varias veces antes de que sea necesario botarlo.*

Fig 3B ~34A

Cateterización Intermitente para la mujer CAREGUIDE continuación...

Introducción del Catéter

Continue a sostener los labios separados. Con la otra mano tome el Catéter por la parte donde apenas acaba la Jalea. Asegúrese que la otra punta del Catéter este dentro del Cofre de Coleccionar Orina.

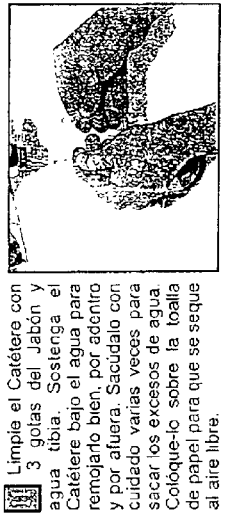

Poco a poco introduja la punta del Catéter en la uretra, empujando hacia arriba y hacia abajo hasta que empieze a orinar. Meta el Catéter otra pulgada más. Asegúrese que la orina este cayendo dentro del cofre.

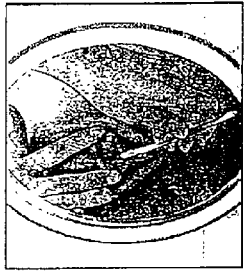

Cuando pare de orinar, suavemente presione hacia abajo en el area de la vejiga para asegurarse que esté vacía. Lentamente saque el Catéter. Si Ud. desea, limpie con papel sanitario la abertura de la uretra para eliminar los residuos de la jalea.

Chequee el nivel de orina dentro del Cofre de Coleccionar Orina. Escriba el número en la Tarjeta Diaria de Orina u otros comentarios que Ud. desee comentar con su doctor o enfermera.

Limpie para la Próxima Vez

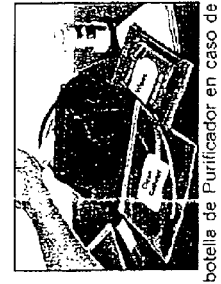

Limpie el Catéter con 3 gotas del Jabón y agua tibia. Sostenga el Catéter bajo el agua para remojarlo bien, por adentro y por afuera. Sacúdalo con cuidado varias veces para sacar los excesos de agua. Colóque-lo sobre la toalla de papel para que se seque al aire libre.

Vacíe el contenido en el Cofre de coleccionar orina. Lave el cofre con 2 gotas de Jabón y agua tibia. Remójelo bien y séquelo. Coloque de vuelta la tapa del pomo de Jalea para Lubricar. Meta de regreso en la caja todos los materiales. Bote en la basura las Telas para Protejer, si están sucias.

El Catéter ya debe de estar seco. Guárdelo dentro de la Bolsa de Catéteres Limpios y ciérrela.

*Su ayudante ya puede quitarse los guantes y lavarse las manos.*

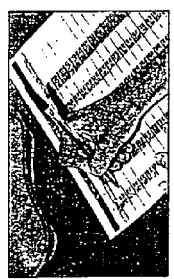

Cuando Viaje. En la Bolsa de cinturon, meta un Catéter dentro de la Bolsa de limpios por cada 4 horas que Ud piensa estar de viaje. También meta los Paños de andar, la Bolsa de usados, Paqueles de jalea Para lubricar, y toallas de papel limpias. Meta la botella de Purificador en caso de que no haya agua. Use una toalla de papel limpia para trabajar sobre ella. Siga todos los pasos (1-13, menos el paso #11) en un lugar privado Cuando termine de usar el Catéter, remójelo si haya agua, y métalo en la Bolsa de usados. Lávese las manos. Cuando esté de vuelta en casa, lave muy bien los Catéteres como en el paso #11, y después guárdelos en la Bolsa de Catéteres Limpios.

Fig 4

SELF CARE DOCUMENTATION
Patient Name

Female Clean Intermittent Catheterization CAREGUIDE™ Step-by-Step  page 1

This sheet is a reduced-size copy of the patient's illustrated, full color instructions. The purpose of this sheet is to confirm that self care training has been carried out by the clinician and understood by the patient and/or caregiver.

Prepare for Care

Get a clean, fresh towel. Wash your hands with the Antibacterial Soap and warm water. Dry your hands on the clean towel. If you have a caregiver to do this procedure for you, they should put on the Gloves after washing their hands.

Spread out two clean paper towels for a work surface. Have the kit near to take out items as they are needed. If you are going to do the procedure on a bed, chair or other furniture, put the Underpad under your buttocks. Take out the Collection Basin and put it between your legs.

The Bulb

Take the Catheter out of the package or "Clean Catheter" Bag and lay it on a clean paper towel within reach.

Flip open the tube of Lubricating Jelly. Be careful, do not let the tube touch the Catheter. Squeeze about 2 inches of Jelly onto the Catheter starting at the tip.

Hold the Catheter so the Jelly touches the paper towel. Roll the Catheter in the Jelly to cover all sides.

Cleaning Down

Wet the Paper Wash Cloth with warm water and squeeze approximately a dime size drop of Antibacterial Soap. Lather up about one half of the Cloth. Put it on a counter of the paper towel.

Lean back with your legs in a frog-leg position. Take out the Mirror. Fold it so it will stand by itself. Adjust the Mirror on the other side of the Basin so you can see your labia and opening of the urethra. It may help to pull back the skin above the clitoris.

Separate the labia with your first and middle finger of one hand while with the other hand, washing from above the opening of the urethra to the area above the anus.

Always wash from the top to the back, each time using a clean area of the Wash Cloth. This prevents germs from the anus area entering the urethra. Wash downward 3 times, then rinse with the half of the Cloth that has no soap. Discard the Wash Cloth. It may be cleaned several times before you throw it away.

Patient Name _____
Provider Name_____
Date _____

44

Check here when Page 1 of training is complete. ☐

Provider initials _____
Patient initials _____

45A

Female Clean Intermittent Catheterization CAREGUIDE™ continued... page 2

Inserting the Catheter

Continue holding the labia apart with one hand. With the other hand pick up the Catheter directly behind the Jelly. Make sure the other end of the Catheter is in the Collectible Container.

Gently insert the Catheter tip into the urethra, pushing backward and upward until the urine begins to flow. Insert the Catheter another inch. Make sure the urine is draining into the Collection Container.

When urine stops flowing, gently push down on the bladder area to make sure the bladder is empty. Slowly pull the Catheter out. You may wish to wipe off any jelly that may remain on the opening of the urethra with toilet paper.

Check the level of urine in the Collection Container. Write the amount on the Urine Record Card and any other comments you may wish to tell your nurse or doctor.

Cleaning for Next Time

Wash the Catheter with 2-3 drops of Antibacterial Soap and warm water. Hold the Catheter under the running tap water to rinse well, inside and out. Shake it gently several times to get off excess water. Place it on a clean paper towel to air dry.

Empty the contents of the Collection Container. Wash the container with 2 drops of Antibacterial Soap and warm water. Rinse it well and dry. Replace the cap on the tube of Lubricating Jelly. Put all the supplies back in the box. Throw away the Underpad if it is soiled.

The Catheter should be dry by this time. Close it inside the Plastic Bag marked "Clean Catheter Storage".

The caregiver may take off the gloves now and wash their hands.

WHEN YOU TRAVEL. In the Fanny Pack, put one clean Catheter in the "Clean Catheter" Bag, for every 4 hours you expect to be away. Also put in the Travel Wipes, the "Used Catheter" Bag, a packet of Lubricating Jelly, and clean paper towels for each catheterization. Take the Alcohol Gel for your handwashing in case there is no water. Follow the same steps above in a place like a bathroom. Starting with step one, wash your hands. Take out a clean paper towel for your work surface. Use a Travel Wipe to clean your urethral opening. Follow the steps above modifying as needed for location. Drain the urine from the Catheter into a toilet if possible. When you remove the Catheter, rinse and store in the "Used Catheter" Bag. Wash your hands. When you are home again, clean the Catheter thoroughly and store in the "Clean Catheter" Bag.

Check here when Page 2 of training is complete. ☐

Provider initials _____
Patient initials _____

45A

45B

We agree that the patient understands these instructions and is ready to carry out self care:

_____ Provider
Signature

_____ Patient
Signature

Fig 5

CAREGUIDE™ URINE RECORD CARD

*Your doctor will tell you how often to record your urine output. Remember to circle AM or PM when you write the time.*

| Date | Time | Quantity | Time | Quantity | Time | Quantity | Time | Quantity | Time | Quantity | Time | Quantity | Time | Quantity | TOTAL |
|---|---|---|---|---|---|---|---|---|---|---|---|---|---|---|---|
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |
| | AM PM | | AM PM | | AM PM | | AM PM | | AM PM | | AM PM | | AM PM | | |

Catherize yourself ___ times a day at ___. Each day drink ___ 8 oz. glasses fluid, but no more than ___ 8 oz. glasses fluid. Your medication is: ___

Patient Name

32

FEMALE CLEAN INTERMITTENT CATHETER SYSTEM

PRIORITY CLAIM

This application claims the benefit of provisional application Ser. No. 60/211,151, filed Jun. 13, 2000.

CROSS-REFERENCE TO RELATED APPLICATIONS

This application is related to the following commonly-owned co-pending patent applications: "A PATIENT DISCHARGE SYSTEM AND METHOD FOR POST BREAST SURGERY CARE," Ser. No. 09/640,680; "METHOD FOR DETERMINING THE CONTENT OF A SELF-CARE KIT," Ser. No. 09/709,917; "PATIENT DISCHARGE SYSTEM AND METHOD FOR SELF-CARE OF A POST-SURGERY DRAIN," Ser. No. 09/779,796; "ANTIBIOTIC DRESSING CHANGE SYSTEM," Ser. No. 09/808,535; "NORMAL SALINE DRESSING CHANGE SYSTEM," Ser. No. 09/808,323; "CIRCUMCISION AFTERCARE SYSTEM," Ser. No. 09/808,335; "MALE CLEAN INTERMITTENT CATHETER SYSTEM," Ser. No. 09/879,321; and "A PATIENT DISCHARGE SYSTEM AND METHOD FOR POST CARDIAC SURGERY CARE" Ser. No. 09/878,671.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

DESCRIPTION

The present invention relates in general to a system and method for using a female catheter and in particular to a system and method for clean intermittent female catheterization by a user or health care provider.

BACKGROUND OF THE INVENTION

It is estimated that urinary catheters are placed in millions of women each year in the United States alone, either due to some illness, infection or malfunction or as part of a medical procedure. Care must be taken to clean the catheter site to reduce the risk of nosocomial infection (i.e., an infection that arises due to a procedure for treating a disorder and unrelated to the disorder itself, also referred to as a "hospital infection").

The most common nosocomial infections are related to or arise from indwelling urinary bladder catheters (i.e., catheters that remain in the urinary tract for a relatively long length of time). The risk of such catheter-related nosocomial infections can be reduced using strict aseptic techniques (i.e., using gloves, disinfectants, antibacterial soaps, etc.) when handling the catheter. Moreover, the risk of infection can further be reduced by only using a catheter intermittently rather than leaving the catheter in place for any length of time. Intermittent use of the catheter in conjunction with clean techniques helps to reduce the risk of catheter-related nosocomial infections and is, moreover, a far more attractive alternative for bladder evacuation to most patients who are candidates for the procedure.

Using a urinary bladder catheter under aseptic conditions in a hospital is routine. However, current medical practice emphasizes getting the patient ambulatory (and out of the hospital) as soon as possible. Consequently, catheterizations or catheter insertions are performed at home by nonprofessionals. These nonprofessionals must be taught clean techniques. However, no know comprehensive devices, apparatus or methods exist for teaching clean techniques or for facilitating such home catheter use for women.

SUMMARY OF INVENTION

The present invention provides a method and system for intermittent catheterization by the patient herself, the patient's caregiver, or a health care provider. The present invention contains apparatus for facilitating at least one catheterization and comprises: (I) at least one female catheter; (II) antibacterial soap; (III) lubricant; (IV) step-by step instructions; and (V) a container, where the above named items are positioned inside the container. It should be appreciated that the present invention may only be used on the order of a physician.

Preferred embodiments of the system contain sufficient apparatus for one month of catheterizations or catheter insertions (approximately 3 to 4 times a day), the antibacterial soap is in liquid form, the lubricant is in gel form, the step-by-step instructions are written in English and Spanish, although other languages (e.g., Polish, French and German for example) are contemplated. One preferred embodiment of the system includes a contents map identifying the contents and the positions of the contents, along with zipper bags, a fanny pack and a protective underpad.

In a more preferred embodiment of the system, the system contains apparatus for at least one month of catheterizations as provided previously and comprises: (I) four intermittent female catheters; (II) thirty-five disposable wipes; (III) one protective underpad; (IV) antibacterial liquid soap; (V) one tube of lubricant; (VI) a mirror; (VII) step-by-step instructions; (VII) clinician step-by-step instructions or self-care documentation; and (IX) a box, wherein the above-named items are positioned inside the box.

The method for intermittent catheterization comprises evacuating the bladder using the apparatus of the present invention in accordance with the detailed step-by-step instructions provided in the system. In a preferred embodiment, the method which is discussed in further detail below generally includes: (I) preparing for intermittent female catheterization; (II) preparing the female catheter; (III) inserting the female catheter; (IV) draining the bladder; (V) recording and disposing of the drainage; and (VI) cleaning and storing the apparatus of the present invention.

The present invention further includes a patient education system for educating users in performing intermittent female catheterization. Specifically, the system includes a system and a black and white copy of the step-by-step instructions without illustrations (referred to herein as self-care documentation). An instructor (i.e., a doctor, nurse, clinician or other medical professional) uses the self-care documentation to educate the user in performing an intermittent female catheterization, preferably using the system of the present invention. The medical professional then keeps the self-care documentation documenting that the user was educated in performing female catheterization.

It is therefore an object of the present invention to provide a system and method for intermittent female catheterization.

It is a further object of the present invention to provide detailed instructions for intermittent female catheterization using the contents of a self-care system.

An additional object of the present invention is to provide self-care documentation to be used by a medical professional in instructing users in the use of the self-care system.

Yet an additional object of the present invention is to provide a patient education system for educating users in performing intermittent female catheterization using the system.

Other objects, features and advantages of the invention will become apparent from the following detailed disclosure, taken in conjunction with the accompanying sheets of drawings, wherein like numerals refer to like parts, components and processes.

BRIEF DESCRIPTION OF THE DRAWINGS

FIGS. 2A and 2B are top plan views of the step-by-step instructions in English of the system of the present invention;

FIGS. 3A and 3B are top plan views of the step-by-step instructions in Spanish of the system of the present invention;

FIG. 4 is a top plan view of the self-care documentation in English used by a medical professional for documenting that the users are instructed in the use of the system of the present invention; and FIG. 5 is a top plan view of the urine record card.

DETAILED DESCRIPTION OF THE INVENTION

It should be appreciated that the figures include one or more of the following trademarks which may be used by the assignee of this application: (a) CAREGUIDE; and (b) CAREGUIDE and DESIGN. It should be appreciated that these trademarks are not part of the present invention.

The present invention is for a system 10 and method for intermittent catheterization of a patient. The user may be the patient herself, the patient's caregiver, an in-home care provider or a healthcare provider which, for brevity, are referred to herein as the "user." The system 10 provides apparatus needed for in-home catheterization.

In general, the intermittent catheterization system 10 contains at least: (I) infection prevention devices (gloves, disposable wipes, zipper bags, alcohol gel (i.e., a waterless cleanser), soap, and protective underpads); (II) insertion devices (female catheter, mirror and lubricant); (III) recording devices (urine record card and collection basin) and (IV) information devices (step-by-step instructions, contents map and self-care documentation) among other items.

Figure 1:
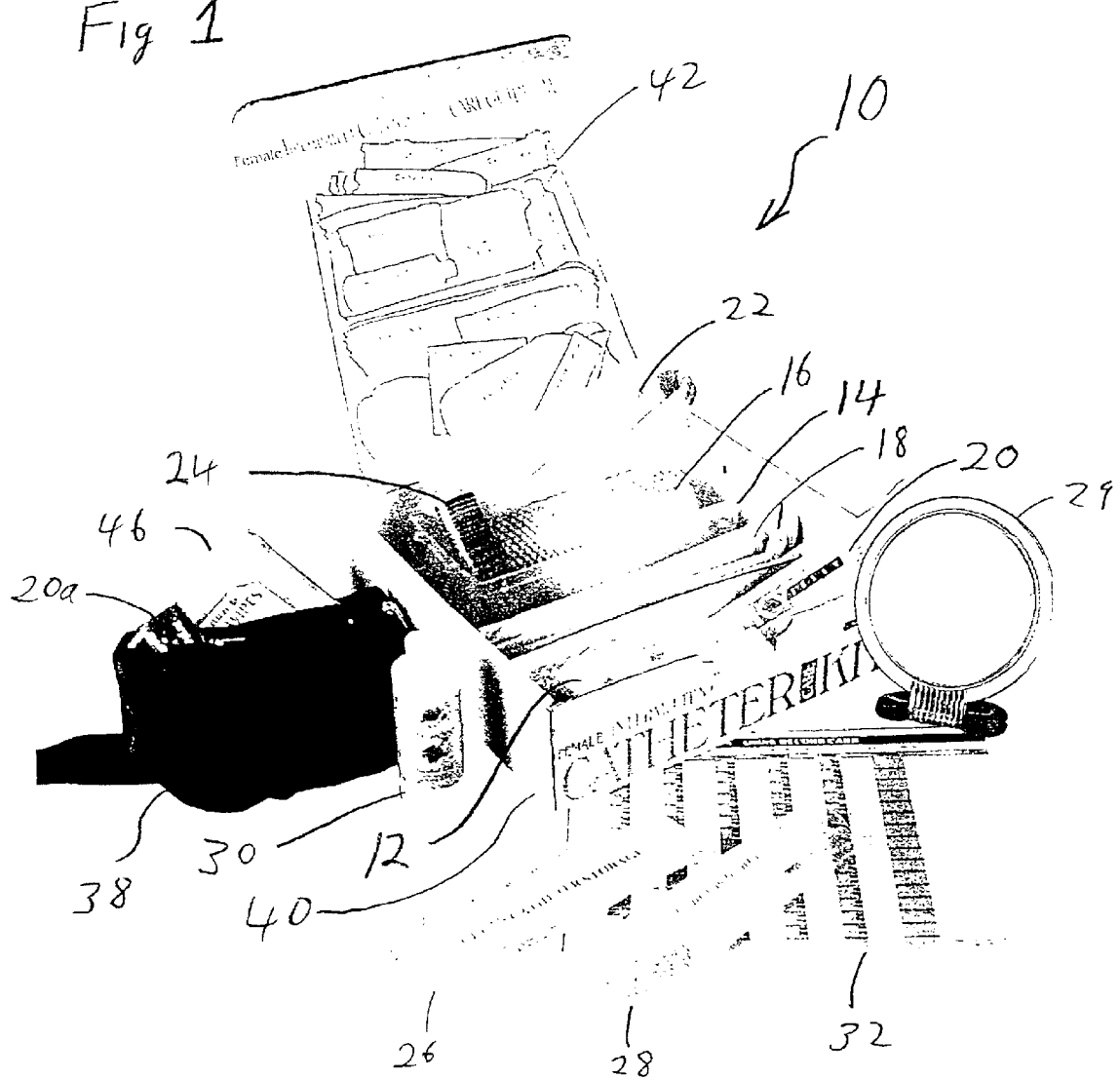
FIG. 1 is a perspective view of the system of the present invention.
Figure 1A:
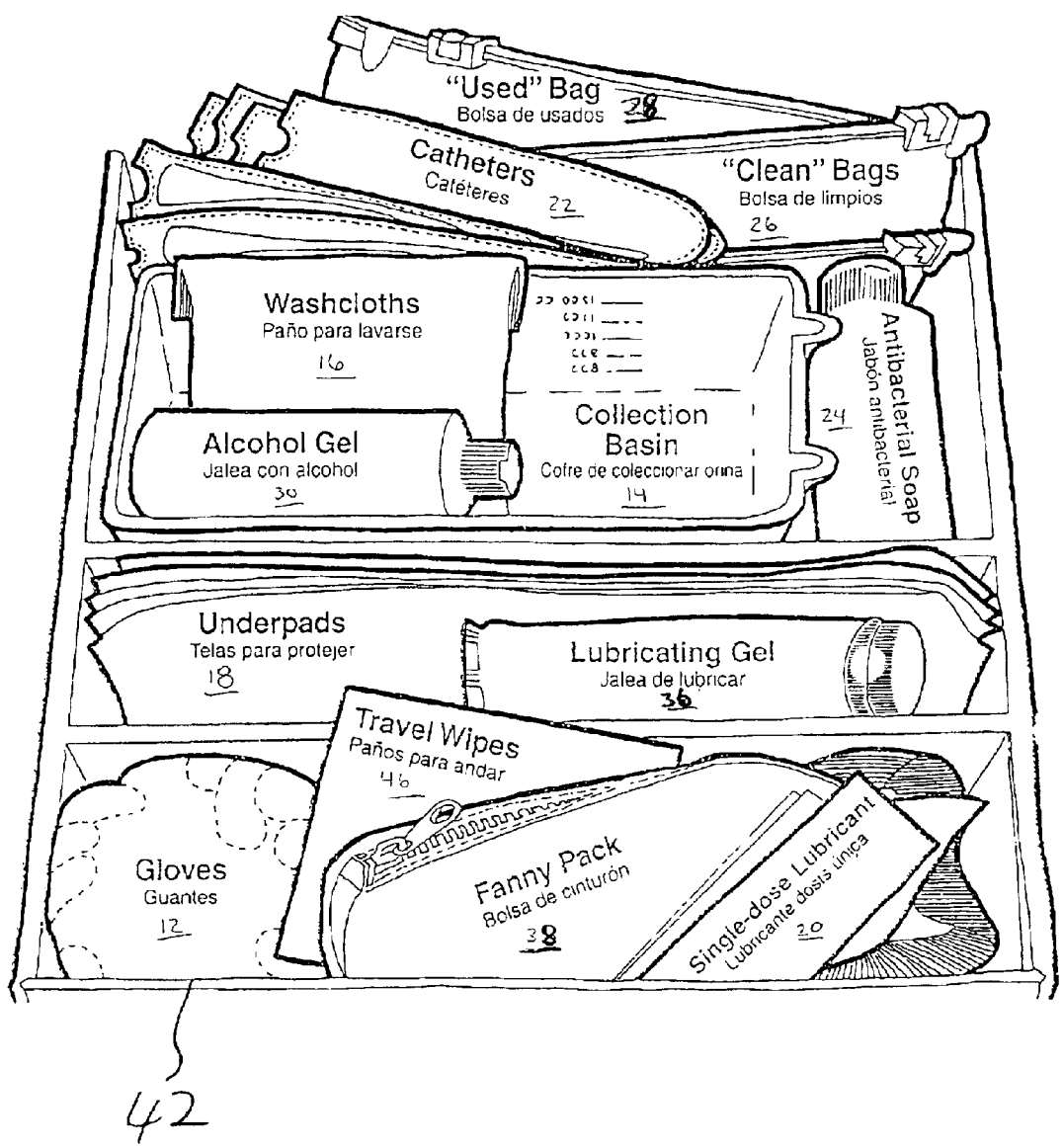
FIG. 1A is a top plan view of the contents map of the present invention.

More specifically, as illustrated by FIGS. 1 and 1A, the intermittent catheterization system 10 of the present invention comprises: (I) gloves 12; (II) a collection basin 14; (III) disposable wipes or washcloths 16; (IV) protective underpad 18; (V) antibacterial soap 24; (VI) lubricating gel 20; (VII) female intermittent catheter 22; (VIII) clean and used zipper bags 26 and 28 respectively; (IX) a mirror 29; (X) step-by-step instructions 34 (not shown in FIG. 1); (XI) self-care documentation 44 (not shown in FIG. 1); and (XII) a container or box 40. It is contemplated that the system 10 may also include a contents map 42 which identify the contents of the container 40 and their position, and one or more waste bags.

In one preferred embodiment, the container 40 contains gloves 12, a plastic collection basin 14 with graduated markings, disposable wipes 16, protective underpads 18, single doses of lubricating gel 20, female catheters 22, antibacterial liquid soap 24, clean catheter zipper bags 26, a used catheter zipper bag 28, alcohol gel 30, a urine record card 32 (illustrated in FIG. 5), a lubricating gel tube 20a, a fanny pack 38, a mirror 29, a travel wipe pack 46, self care documentation 44, and step-by-step instructions 34 as revealed by FIGS. 1, 2A and 2B, and 3A and 3B. It should be appreciated that system 10 could be provided to the patient in a box, tray, bag, container or any other suitable content holder device 40. A box is preferred as it is strong enough to protect the contents of the system 10 and yet is suitable for shipping and storing. If a bag, tray, container or other content holding devices are used, a contents map 42 may or may not be included with system 10.

In one preferred embodiment, a urologist, clinician or other medical professional provides system 10 to the user, although it is contemplated that the user could obtain system 10 through other means but only under a medical professional's care. System 10 includes extremely detailed and specific step-by-step instructions 34 as illustrated in FIGS. 2A and 2B that the user uses with the intermittent female catheterization system 10 (specific step-by-step instructions in Spanish are illustrated in FIGS. 3A and 3B). System 10 also includes the self-care documentation 44 the medical professional uses to document or record the instructions provided to the user in the use of the intermittent female catheterization system 10 as illustrated in FIG. 4. A difference between the two sets of instructions is that the instructions in FIG. 4 are in black and white and include acknowledgment sections 45A and 45B, while the instructions in FIGS. 2A and 2B are illustrated in color (not shown) for ease of use by the patient. It is also contemplated that system 10 could include an instructional video, training the user in the use of the system 10.

In one preferred embodiment, system 10 includes sufficient apparatus for one month of catheter insertions, the antibacterial soap 24 is in a liquid form, the lubricant 20 is provided in a gel or ointment form, and the step-by-step instructions 34, and the contents map 42 (if included) are written in English. While not necessary, one preferred embodiment also includes one or more gloves 12, disposable wipes 16 and a protective underpad 18. It should be appreciated that a user could order a refill of the disposable apparatus of the present invention using an order form provided with the apparatus of the present invention.

In a more preferred embodiment of the system, system 10 includes apparatus for at least one month of catheterization and comprises: (I) 10 gloves 12; (II) one collection basin 14; (III) 35 disposable wipes 16; (IV) 3 protective underpads 18; (V) 10 single tubes of lubricating gel 20a; (VI) 4 female intermittent catheters 22; (VII) antibacterial liquid soap 24; (VIII) 4 clean catheter zipper bags 26; (IX) one used catheter zipper bag 28; (X) 4 oz of alcohol gel 30; (XI) one urine record card 32; (XII) one lubricating gel tube 36; (XIII) a fanny pack 38; (XIV) a mirror 29; (XV) one pack of travel wipes 46; (XVI) self-care documentation 44; (XVII) detailed step-by-step instructions 34; (XVIII) a contents map 42; and (XIX) container or box 40 wherein the above-named items are positioned inside the box 40.

The system 10 includes apparatus necessary for intermittent female catheterization in accordance with the method. The system 10 organizes the apparatus in an easy-to-find format. The step-by-step instructions 34 indicate when an item is first required during the method and should be removed from the container 40 (preferably using red text to indicate when an item is first required). Using the step-by-step instructions 34 and the contents map 42, users can easily identify when each item is required in the method and readily find it in the container 40. It should be appreciated that the items and step-by-step instructions 34 could be color coded and/or use icons making identifying each item even easier. For example, the antibacterial soap 24 could be identified by a bubbles icon and blue coloring corresponding to a bubbles icon and blue color in the step-by-step instructions 34.

The method of the present invention generally comprises using the system 10 in accordance with the detailed step-by step instructions 34. In a preferred embodiment, the method generally includes: (I) preparing for intermittent female catheterization; (II) preparing the female catheter; (III) inserting the female catheter; (IV) draining the bladder; (V) recording and disposing of the drainage; and (VI) removing the female catheter and cleaning and storing the apparatus.

Preparing for Intermittent Female Catheterization
(Step I)

The first step of the method of the present invention, is illustrated by FIGS. 2A and 2B and includes preparing and caring for the female catheterization site. Preparing and caring for the female catheterization site includes: (I) obtaining a clean, fresh towel; (II) washing using the antibacterial liquid soap 24 and warm water, and using the clean towel for drying; (III) finding a safe, flat, uncluttered, solid surface; (IV) putting on the gloves 12 only if the catheterization is being performed by a user other than the patient which includes: (a) taking a pair of gloves 12 out of the box 40; and (b) putting them on; (V) preparing the surface which includes: (a) obtaining two clean, fresh paper towels; (b) opening the two paper towels; (c) placing the opened paper towels on the surface; (d) taking a protective underpad 18 out of the box 40; (e) opening the protective underpad 18; and (f) placing the opened protective underpad 18 under the patient's buttocks and near the opened paper towels; (VI) cleaning the catheter site which includes: (a) taking a paper wash cloth or disposable wipe 16 out of the box 40; (b) taking the container of antibacterial soap 24; (c) squeezing out approximately one dime's worth (i.e., about one or two drops) of soap 24 onto the center of the wipe 16; (d) creating a lather on approximately one half of the wipe 16; (e) leaning back in a frog-leg position; (f) taking out the folding mirror 29; (g) folding the mirror 29 so that it stands by itself; (h) adjusting the mirror 29 to view the catheterization site including the opening of the urethra; and (i) gently washing the site using the wipe 16, the soap 24 and warm water, washing the site from the top to the back; (j) washing the site three times, using a clean area of the wipe 16; and (k) rinsing using the other half (unlathered half) of the wipe 16; (VII) throwing the wipe 16 away; (VIII) washing using the antibacterial soap 24 as described previously. It should be appreciated that step (VIII) can be skipped if the user is wearing gloves 12.

Preparing The Female Catheter (Step II)

The second step of the method as illustrated includes inserting the female catheter 22 into the urethra. Inserting the female catheter 22 includes: (I) taking a female catheter 22 out of the box 40; (II) laying the catheter 22 on the paper towels; (III) take the collection basin 14 out of the box 40 and placing it near the paper towels; (IV) applying the lubricating gel 20 which includes: (a) taking the lubricating gel tube 20 out the box 40; (b) flipping open the cap of the tube 20; (c) squeezing 3 inches of lubricating gel 20 onto the catheter 22 starting at the tip, being careful not to touch the catheter 22 with the tube 20; (d) rolling the catheter 22 in the lubricating gel 20 so that all sides are covered; (e) lifting the catheter 22 away from the paper towel and laying the wide end of the catheter 22 in the collection basin 14; and (f) moving the basin 14 close to the user so that the wide end of the catheter 22 is not accidentally pulled out of the basin 14.

Inserting the Female Catheter (Step III)

The third step of the present invention comprises inserting the catheter 22 into the urethra. Inserting the catheter 22 comprises: (I) sitting on the underpad 18; (II) separating the labia with one hand; (III) picking up the catheter 22 near the tip with the other hand, keeping the other end in the basin 14; (IV) having the patient taking a deep breath; (V) gently inserting the tip of catheter 22 into the urethra; (VI) pushing backward and upward until a bit (i.e., at least a drop) of urine appears; and (VII) slowly pushing the catheter 22 in one inch more.

Draining the Bladder (Step IV)

The fourth step of the method comprises draining the site (i.e., the bladder) forming a drainage. Draining the catheter site using the catheter 22 comprises: (I) placing or holding the basin 14 in proximity to the widened (i.e., uninserted) end of the catheter 22; (II) making sure the wide end of the catheter 22 is in the basin 14; (III) holding the catheter 22 in place and emptying the bladder into the basin 14; (IV) making sure the urine is running into the basin 14; (V) pushing down on the bladder, making sure it is empty; and (VI) slowly pulling the catheter 22 out when the bladder is empty (i.e., the urine stops).

Recording and Disposing of the Drainage (Step V)

The next step of the method includes recording and disposing of the drainage. This step includes: (I) recording the amount of the drainage, including: (a) measuring the drainage level using the markings on the basin 14; (b) writing this amount on the urine record card 32 illustrated FIG. 5; (c) noticing the color and smell of the drainage; and (d) recording the color and smell (and anything else to tell the doctor) on the urine record card 32; and (II) disposing of the drainage, preferably emptying the basin 32 in a toilet.

Cleaning and Storing the Apparatus (Step VI)

The next step includes completing the intermittent catheterization in accordance with the method. Completing the catheterization includes: (I) cleaning the used catheter, which includes: (a) washing the used catheter 22 with two or three drops of the antibacterial soap 24 and warm water; (b) holding the catheter 22 under running tap water, rinsing it well inside and out; (c) shaking the catheter 22 gently several times to remove any excess water; and (d) placing the catheter 22 on a clean, fresh paper towel to air dry; (II) removing any gel left on the female catheterization site using toilet paper or other soft wipe; (III) cleaning the basin 14, which includes: (a) washing the basin 14 using two drops of antibacterial soap 24 and warm water; (b) rinsing the basin with warm water; and (c) placing the basin 14 on clean, fresh paper towel to air dry; (IV) closing the cap on the lubricating gel tube 20; (V) placing all the apparatus back in the box 40; (VI) placing the dry catheter 22 inside a clean catheter zipper bag 26, zipping it closed; (VII) placing the clean catheter zipper bag 26 in the box 40; (VIII) placing the dry basin 14 in the box 40; (IX) placing the underpad 18 in the box 40 if clean, or throwing it away if dirty; and (X) disposing of the wipe 16 and the paper towels.

It should be anticipated that the patient is not bed bound, but able and willing to get around. One preferred embodiment of the present invention includes a fanny pack 38 that enables users to travel. As illustrated in FIGS. 2A and 2B, method provides that, for every four hours of travel, the fanny pack 38 should include: (I) one clean catheter 22 in the clean catheter zipper bag 26; (II) one packet of lubricating gel 20a; and (c) two clean paper towels. The fanny pack 38 should also include the pack of pre-wet travel wipes 46, the used catheter zipper bag 28, and the alcohol gel 30 for handwashing in case water is not available.

When catheterization is required, the user should find a place (preferably a bathroom) and follow Steps I–VI above, using clean paper towels for a clean work surface. After removing the catheter 22 in Step V, the user should rinse it off if possible and store it in the used catheter zipper bag 28, placing the bag 28 in the fanny pack 38. The user should then wash as described above in Step I. The used catheters may be cleaned completely upon returning home.

The present invention includes teaching or instructing the user in the use of system 10. System 10 includes a set of extremely detailed, step-by step instructions 34, as illustrated in FIGS. 2A, 2B, 3A and 3B and self-care documentation 44 illustrated in FIG. 4.

Federal, state and local regulatory agencies require that the medical professional maintain complete records, including records to training provided to individuals. The medical care professional uses the self-care documentation to document providing the instructions to the patient or user on the use of the method and system 10 as illustrated in FIG. 4. The instructions enables the medical care professional to ensure that the training is complete, providing a signature box or acknowledgement areas 45A and 45B for the user to indicate that they received and understand the instructions. This documentation 44 is maintained by the clinician or a medical provider as part of the clinical record, where they may be used for accreditation and/or legal purposes.

The present invention further contemplates a patient education system for educating users in performing intermittent female catheterization. The system includes the system 10 and the self-care documentation 44. The present invention is only used on the order of a physician. An instructor (i.e., a doctor, nurse, clinician, other medical profession, or any individual trained to educate users in performing female catheterization) uses step-by-step instructions 34 or 44 to teach the users to perform a female catheterization, preferably using the system 10. The instructor takes the user through the process of performing a female catheterization step-by-step, and may even demonstrate specific procedures using specific items in the system 10. For example, it is contemplated that the instructor could demonstrate how to apply lubricating gel to the catheter 22, clean the catheter 22, record drainage, etc. It should be appreciated that the instructor could use a model to demonstrate how to insert the female catheter 22, drain the bladder and remove the catheter 22.

It should be appreciated that the system 10 may contain sufficient apparatus for one or more catheter insertions; for example, apparatus for two, three, four or more months of catheter usage are contemplated. Further, it should be appreciated that refills for system 10 may be provided. In a preferred embodiment, a reorder form may be provided in system 10.

While the present invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the claims. It is thus to be understood that modifications and variations in the present invention may be made without departing from the novel aspects of this invention as defined in the claims, and that this application is to be limited only by the scope of the claims.

The invention is hereby claimed as follows:

1. A patient education system for educating users in intermittent female catheterization, said system comprising:
a female catheterization system including at least one female catheter wherein said female catheterization system contains:
(a) ten gloves;
(b) a collection basin;
(c) thirty-five disposable wipes
(d) three protective underpads;
(e) four female catheters;
(f) ten single doses of lubricant gel;
(g) antibacterial liquid soap;
(h) four clean catheter zipper bags;
(i) a used catheter zipper bag;
(j) a container of alcohol gel;
(k) a urine record card;
(l) a lubricating gel tube;
(m) a mirror;
(n) a fanny pack;
(o) step-by-step instructions;
(p) a box wherein items (a) through (o) are positioned inside the box; and
self-care documentation which an instructor uses to educate the users in performing intermittent female catheterization using the female catheterization system.

2. The patient education system of claim 1, wherein the self-care documentation includes at least one acknowledgement section for documenting instructions provided to the users.

3. The patient education system of claim 1, which further includes a set of step-by-step instructions used by the users in performing intermittent female catheterization.

4. The patient education system of claim 1, wherein said female catheterization system contains apparatus for at least one month of catheterizations.

5. A system for facilitating intermittent female catheterization, said system comprising:
a plurality of infection prevention devices;
at least one female insertion device wherein said female insertion device includes at least one female catheter, one mirror and lubricant; and
at least one recording device which enables a user to record an amount of drainage from a catheter site.

6. The system of claim 5, wherein said recording device includes a collection basin and a record card.

7. The system of claim 5, which includes at least one information device.

8. The system of claim 7, wherein said information device includes at least one set of step-by-step instructions.

9. The system of claim 8, wherein said information device includes at least one contents map.

10. The system of claim 7, wherein said information device includes self-care documentation for documenting instructions provided to the user in the use of the system.

11. The system of claim 5, wherein said system contains sufficient apparatus for a plurality of catheterizations.

12. A system for intermittent female catheterization used by a user and containing apparatus for at least one catheterization, said system comprising:
- (a) at least one female catheter;
- (b) antibacterial soap;
- (c) lubricant;
- (d) a mirror;
- (e) at least one set of step-by-step instructions; and
- (f) at least one container for holding the system.

13. The system of claim 12, which includes self-care documentation including at least one acknowledgement section for documenting instructions provided to the user in the use of the system.

14. A method for intermittent catheterization by a user comprising inserting a catheter with the system of claim 12.

15. A system for intermittent female catheterization used by a user for a plurality of catheter insertions, said system comprising:
- (a) ten gloves;
- (b) a collection basin;
- (c) thirty five disposable wipes
- (d) three protective underpads;
- (e) four female catheters;
- (f) ten single doses of lubricant gel;
- (g) antibacterial liquid soap;
- (h) four clean catheter zipper bags;
- (i) a used catheter zipper bag;
- (j) a container of alcohol gel;
- (k) a urine record card;
- (l) a lubricating gel tube;
- (m) a mirror;
- (n) a set of step-by-step instructions; and
- (o) a box wherein items (a) through (n) are positioned inside the box.

16. The system of claim 15, which includes self-care documentation for documenting instructions provided to the user in the use of the system.

17. A system for intermittent female catheterization used by a user and containing apparatus for at least one catheterization, said system comprising:
- (a) at least one female catheter;
- (b) lubricant;
- (c) a mirror;
- (d) at least one set of step-by-step instructions; and
- (e) at least one container for holding the system.

18. The system of claim 17, which includes self-care documentation including at least one acknowledgement section for documenting instructions provided to the user in the use of the system.

19. A method for intermittent catheterization by a user comprising inserting a catheter with the system of claim 17.

* * * * *